US011351030B2

(12) United States Patent  
Kuhn et al.

(10) Patent No.: US 11,351,030 B2  
(45) Date of Patent: Jun. 7, 2022

(54) SURGEON SPECIFIC BONE PLATES

(71) Applicant: Stryker European Operations Holdings LLC, Kalamazoo, MI (US)

(72) Inventors: Markus Kuhn, Ebringen (DE); Reinhard Rübecamp, Weckolsheim (FR); Andy Perrin, Kalamazoo, MI (US); Verena Heizmann, Freiburg (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 176 days.

(21) Appl. No.: 16/913,522

(22) Filed: Jun. 26, 2020

(65) Prior Publication Data

US 2021/0007849 A1 Jan. 14, 2021

Related U.S. Application Data

(60) Provisional application No. 62/872,786, filed on Jul. 11, 2019.

(51) Int. Cl.
*A61F 2/28* (2006.01)
*A61F 2/30* (2006.01)
*A61B 17/80* (2006.01)

(52) U.S. Cl.
CPC ........ *A61F 2/2803* (2013.01); *A61B 17/8071* (2013.01); *A61F 2/30942* (2013.01); *A61F 2002/30943* (2013.01)

(58) Field of Classification Search
CPC ............................ A61F 2/2803; A61F 2/30942
See application file for complete search history.

(56) References Cited

U.S. PATENT DOCUMENTS

| | | | |
|---|---|---|---|
| 4,966,599 | A | 10/1990 | Pollock |
| 5,413,577 | A | 5/1995 | Pollock |
| 5,746,742 | A | 5/1998 | Runciman et al. |
| 6,283,969 | B1 | 9/2001 | Grusin et al. |
| 6,978,188 | B1 | 12/2005 | Christensen |
| 7,963,979 | B2 | 6/2011 | Phillips et al. |
| 8,126,234 | B1 | 2/2012 | Edwards et al. |
| 8,734,492 | B2 | 5/2014 | Mohr et al. |

(Continued)

FOREIGN PATENT DOCUMENTS

| | | |
|---|---|---|
| EP | 2563244 B1 | 7/2016 |
| WO | 2014089285 A1 | 6/2014 |

OTHER PUBLICATIONS

Synthes CMF, "MatrixMANDIBLE Preformed Reconstruction Plates", Copyright 2012, 4 pages.

*Primary Examiner* — Jason-Dennis N Stewart  
(74) *Attorney, Agent, or Firm* — Lerner, David, Littenberg, Krumholz & Mentlik, LLP

(57) ABSTRACT

A method of designing a set of contoured implants for fixation to a bone of a patient, includes obtaining a set of virtual bone models of the bone, selecting a plurality of points on an outer surface of each virtual bone model in the set of virtual bone models, manufacturing a set of implants, each implant corresponding to a respective virtual bone model and having fixation holes corresponding to the selected plurality of points on the outer surface of the respective virtual bone model, contouring each implant in the set of implants and selecting a contoured implant from the set of implants for fixation to the bone of the patient such that the selected contoured implant corresponds to a size of the bone of the patient.

20 Claims, 8 Drawing Sheets

(56) References Cited

U.S. PATENT DOCUMENTS

| | | |
|---|---|---|
| 9,411,939 B2 | 8/2016 | Furrer et al. |
| 9,603,670 B2 | 3/2017 | Brianza et al. |
| 9,715,563 B1 | 7/2017 | Schroeder |
| 10,192,002 B2 | 1/2019 | Benker et al. |
| 2015/0051876 A1 | 2/2015 | Rueber et al. | ated design and subsequent manufacture of a set of surgeon specific bone plates.
SURGEON SPECIFIC BONE PLATES

CROSS-REFERENCE TO RELATED APPLICATIONS

This application claims the benefit of the filing date of U.S. Provisional Patent Application No. 62/872,786 filed Jul. 11, 2019, the disclosure of which is hereby incorporated herein by reference.

BACKGROUND OF THE INVENTION

The present disclosure generally relates to surgical implants in the form of bone plates, and more particularly, to the computer-implemented design and subsequent manufacture of a set of surgeon specific bone plates.

Orthopedic procedures often require the implantation of a plate to stabilize a fractured bone during the healing process, whether the fracture be naturally occurring or surgeon-created to achieve a desired correction. Plates are typically implanted in locations where a cast cannot be used such as the jaw, nose, eye sockets and skull, but can also be implanted to stabilize small bones such as bones of the hands and feet and long bones such as those of the arms and legs. Proper healing of bone depends, in part, upon the fit of the plate to the bone. A plate that does not properly fit the bone may slow or nullify the healing process, and may cause a patient unnecessary pain and discomfort.

Conventional plates, or stock plates, are typically planar and shaped to the general anatomy of the bone to which the plate is to be applied. Mandibular stock plates, for example, are generally flat and straight or flat and L-shaped to correspond to the general shape of the mandible. Accordingly, when implanting the stock plate, the surgeon must intraoperatively bend the plate around the mandible of a patient to conform the plate to the mandible before securing the plate to the bone. Proper fit of the plate is thus dependent upon the conformity of the plate to the mandible of the patient as well as the skill of the surgeon performing the operation. The intraoperative bending process may extend the length of the operation, which may lead to various surgical complications.

Patient specific plates, on the other hand, are pre-operatively manufactured to fit the anatomy of a specific patient, and thus, are designed to not require intraoperative manipulation. For example, U.S. Pat. Pub. No. 2015/0051876 discloses a technique for generating a plate design from medical imaging data representative of the anatomy of the patient to create a template of a plate that is contoured to fit the mandible of the patient. The imaging data may be obtained from a computerized tomography (CT) scan, X-ray, MRI or other known imaging techniques. Patient specific plates, however, are not without drawbacks. First, it is expensive and time consuming to pre-operatively customize plates to an individual patient. Secondly, CT scans expose the patient to radiation which can be hazardous to the health of the patient if overused.

Therefore, there is a need for an improved technique of generating plates that eliminates the necessity of medical imaging and that facilitates proper fit of the plate to the bone.

BRIEF SUMMARY OF THE INVENTION

In accordance with a first aspect of the present invention, a method of designing a set of contoured plates for fixation to a bone is provided. The method includes obtaining a set of virtual bone models of the bone, selecting a plurality of points on an outer surface of each virtual bone model in the set of virtual bone models, and manufacturing a set of bone implants. Each implant corresponds to a respective virtual bone model and has fixation holes that correspond to the selected plurality of points on the outer surface of the respective virtual bone model. The method further includes contouring each implant in the set of bone implants and selecting a contoured bone implant from the set of bone implants for fixation to the bone of the patient, whereby the selected contoured bone implant corresponds to a size of the bone of the patient.

In accordance with another aspect of the invention, a method of designing a set of contoured bone plates for fixation to a bone includes obtaining at least three different sized virtual bone models of the bone, selecting a plurality of points on an outer surface of each virtual bone model and manufacturing bone implants. Each implant corresponds to a respective virtual bone model and has fixation holes that correspond to the selected plurality of points on the outer surface of the respective virtual bone model. The method further includes contouring each of the manufactured bone implants and selecting a contoured bone implant for fixation to the bone of the patient, whereby the selected contoured bone implant corresponds to a size of the bone of the patient.

DETAILED DESCRIPTION

The method described herein may be implemented using software functioning in conjunction with a programmed microprocessor, an Application Specific Integrated Circuit (ASIC), a Digital Signal Processor (DSP) or a general purpose computer. It will be appreciated that while the following embodiments will primarily be described in the context of methods, the present disclosure may also be embodied in a computer program product which can be loaded to run on a computer or a distributed computer system including one or more processors and one or more memories functioning as storage, whereby the one or more memories are encoded with one or more programs that may perform the methods, functions and steps disclosed herein. While the methods are described herein in connection with the design and subsequent manufacture of mandibular plates, it will also be appreciated that these concepts may be equally applicable to the design and manufacture of plates for other bones and implants in general.

Figure 1:
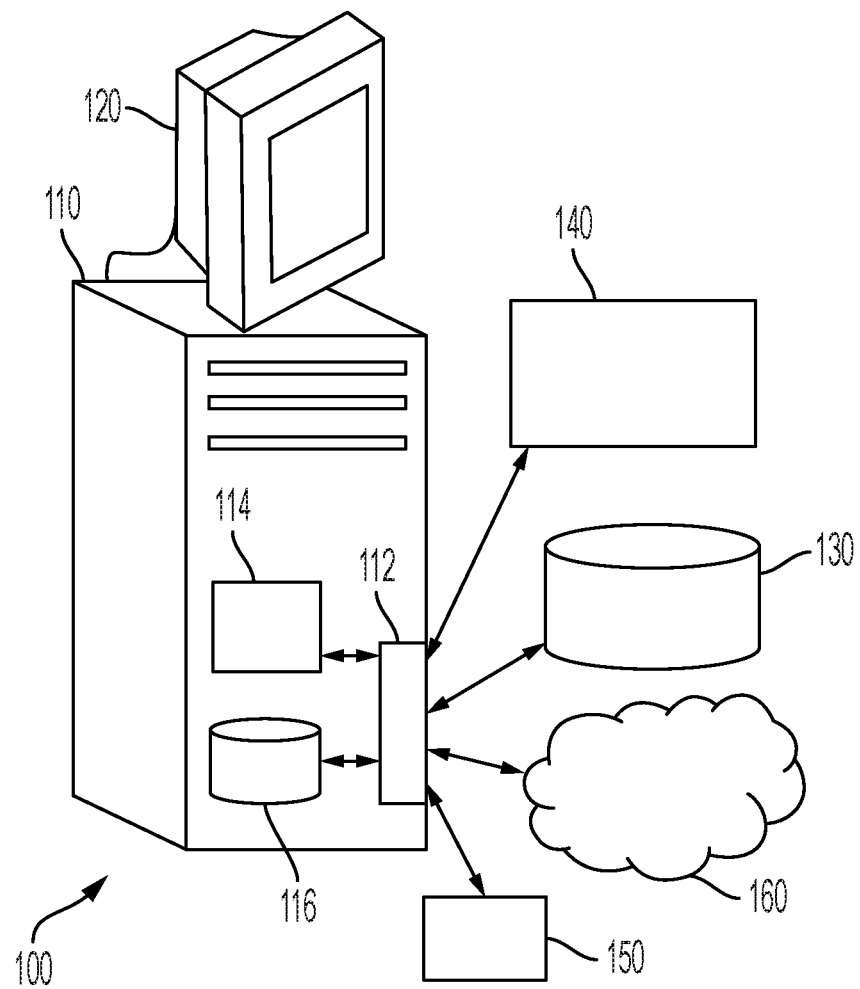
FIG. 1 schematically illustrates a system for designing and manufacturing bone plates in accordance with an embodiment of the present invention.

FIG. 1 schematically illustrates an exemplary system 100 adapted to design and manufacture plates. System 100 includes a computing device 110 (such a personal computer), a display device 120 (such as a monitor), a storage 130 (such as hard disk or a semiconductor memory in which a mean model bone database is provided) and a manufacturing device 140 (such as a programmable machining device). System 100 further includes at least one user-operable input device 150 (such as a keyboard, a mouse or a trackball) for generating or triggering the generation of user interaction signals. In one implementation, display device 120 and input device 150 may be integrated into a touchscreen.

Computing device 110 includes an interface 112, at least one processor 114 (such as a Central Processing Unit, CPU) and a storage 116 (such as a hard disk or a semiconductor memory). Interface 112 is configured as an input/output interface for establishing a communication between computing device 110 on the one hand and, on the other hand, display device 120, storage 130, manufacturing device 140, input device 150 and a computer network 160 (such as a Local Area Network, LAN, and/or the Internet). Interface 112 can be realized in the form of one or more hardware components, one or more software components or a combination of one or more hardware components and one or more software components.

System 100 is configured to design anatomically pre-shaped, surgeon specific plates, and may be operated in whole or in part by a manufacturing company, a hospital, a healthcare professional, an implant design company, another third party, or by any combination of any of the above parties. Each of the parties set forth above and/or other relevant parties may operate any number of respective computers and may communicate internally and externally using any number of networks including, for example, wide area networks (WAN's) such as the Internet or local area networks (LAN's).

As used herein, the term "anatomically pre-shaped" means that the plate is contoured in 3-dimensions to have a shape that substantially conforms to a mean model of the bone to which the plate is to be fixated. Each of the mean models are derived from data of a particular anatomical bone from a population-based design environment featuring a large database of bone morphology including, size, shape and contour of the bone, drawn from a diverse patient population. For example, system 100 may be used to design a mandibular plate that is shaped and contoured to fit the mean (e.g., average) mandible of a general or particular segment of the population. In other words, the manufactured plate is not patient specific as it is not designed for a particular patient. Instead, the plate is pre-operatively designed to substantially fit a majority of the population, or a majority of a particular segment of the population, such that only minor intraoperative adjustments may be needed for proper fitting.

As used herein, the term "surgeon specific" means that particular features of the plate design, for example, aperture placement and plate thickness may be designed based upon the preference of the end user (e.g., the surgeon). It will be appreciated that different surgeons have different approaches for performing the same surgery, and as such, may have different preferences for particular features of the plate, for example, the location of the apertures that receive the bone fastener for fastening the plate to the bone. It is expressly noted that the term surgeon specific means that the plate is designed to a particular preference of the end user (e.g., the surgeon) but that the plate may be designed by the surgeon, the manufacturing company, the hospital, another healthcare professional, the implant design company, or any other third party pursuant to the instructions of or on behalf of the surgeon or other end user performing the operation.

Storage 130 includes a database upon which mean model bone data is stored. The database may contain mean model bone data for a variety of anatomical bones such as the mandible, maxilla, the zygomatic bone, the cranium etc. Each of these anatomical bones may include a plurality of mean models based upon the size of the bone. With respect to the mandible, for example, the database may include a small mean model, a medium mean model and a large mean model. In this exemplary embodiment, the overall population is segmented into classes by the size of the mandible. For example, the small mean model may be the mean model of the smallest 30% of mandibles in a particular population, the medium mean model may be the mean model of the middle 40% of mandibles in the population and the large mean model may be the mean model of the largest 30% of mandibles of the population. As a result, when manufactured, the small plate will closely approximate and fit the mandible of the smallest 30% of the population, the medium plate will closely approximate and fit the mandible of the middle 40% of the population and the large plate will closely approximate and fit the mandible of the largest 30% of the population. In other embodiments, it will be appreciated that the database may include fewer than three mean models or greater than three mean models of a particular bone. It will also be understood that the general population can be adjusted such that each class has fewer or greater percentages of the overall population in each class. Moreover, each class may be further segmented into subclasses to account for age, race or other factors that will provide a more accurate mean model of a particular patient's mandible. The database may also be used to store information obtained from parties such as healthcare professionals and implant manufacturers.

Figure 2:
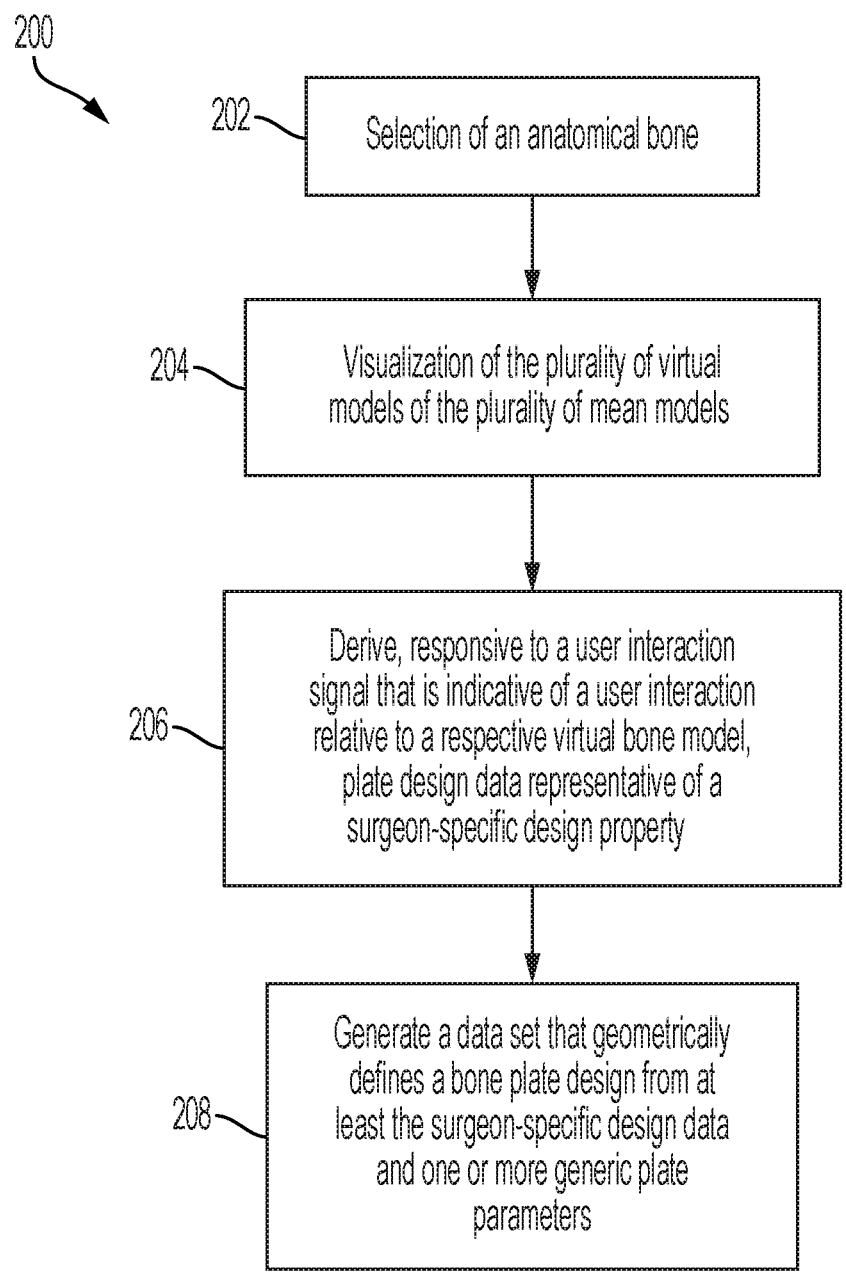
FIG. 2 is a flow diagram illustrating a method for designing the plates.
Figure 3:
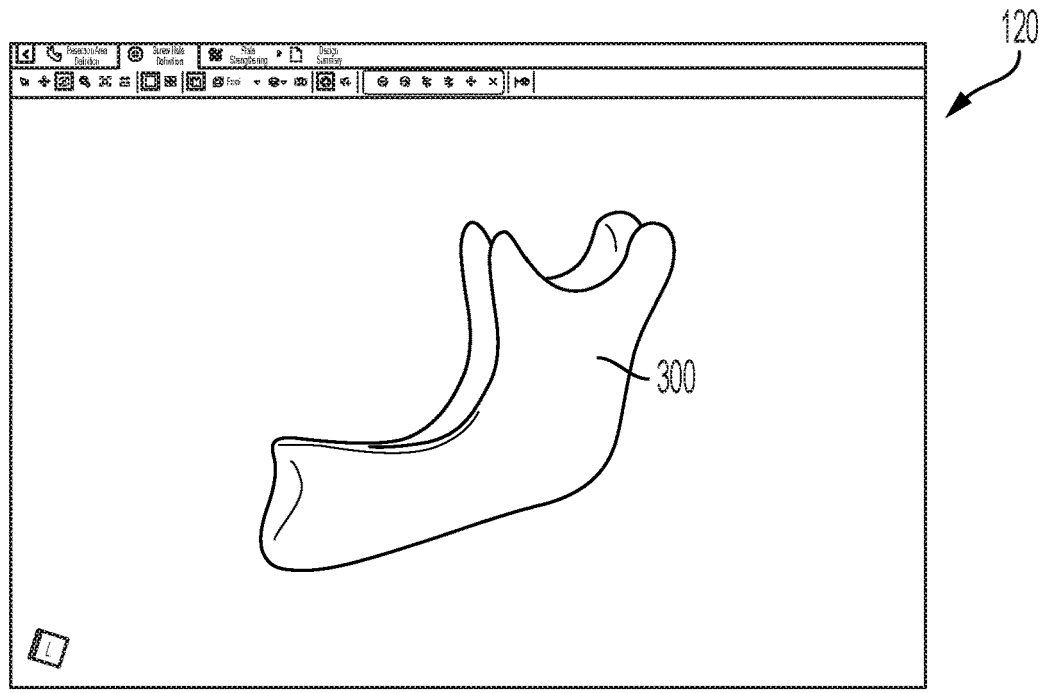
FIG. 3 is a schematic diagram of a display screen displaying a virtual mean model of a mandible bone.

FIG. 2 is a flow diagram 200 illustrating an implemented method of designing a set of surgeon-specific, anatomically pre-shaped bone plates using system 100. First, the user selects the anatomical bone 202 to which the plate is to be fixed. Upon selecting the bone, the database and processor 114 will cause the plurality of mean models for the selected bone to be visualized on display device 120 as virtual three-dimensional models of the selected bone 204. The virtual bone models may be displayed sequentially such that a single virtual model is displayed at a time as shown in FIG. 3.

In a next step 206, a software-based plate design functionality is executed. The plate customization functionality may be stored as program code in the internal storage 116 or the external storage 130. When executed by the processor 114, the plate design functionality derives, responsive to a user interaction signal that is indicative of a user interaction relative to the virtual bone model, plate design data representative of a surgeon-specific design property.

The user interaction may take place via the input device 150. As an example, the user interaction may involve moving a (virtual) pointer, on the display device 120, relative to the model of the bone to a desired portion and pressing a key of the keyboard, a mouse button or a trackball button. The plate design data may then be derived based on the position of pointer relative to the model of the bone (e.g., in the coordinate system of the bone model and/or the shape data) at the time when the key or button is pressed. As an example, the plate design data thus derived may be indicative of the position of characteristic features of the plate to be designed, such as one or more fixation openings, thickness of the plate, one or more plate segments, and so on. The resulting plate design data may be stored in the internal storage 116, the external storage 130 or both storages 116, 130. Additionally, or as an alternative, the plate design data may be transmitted, via the computer network 160, to a remote computing device (not shown in FIG. 1).

In a further step 208, the processor 114 generates a data set geometrically defining the plate design from at least the surgeon-specific design data and one or more generic plate parameters. The generic plate parameters may be indicative of generic dimensions and/or generic design properties of the plate. The processor may process further data in order to generate the plate design data, such as one or more of the shape data, reconstruction data and resection data. The resulting plate design data may in one example be indicative of the geometric dimensions and the geometric features of the customized plate. The shape data (e.g., in the form of surface data) is derived from the virtual mean model so as to define a plate contour.

Having described the basic operation of system 100, the operation will now be described in more detail. The technique will be described in the context of designing and manufacturing a surgeon specific mandibular reconstruction plate, however, it will be appreciated that plates other than mandibular reconstruction plates may be designed and manufactured using these principles.

Figure 4A:
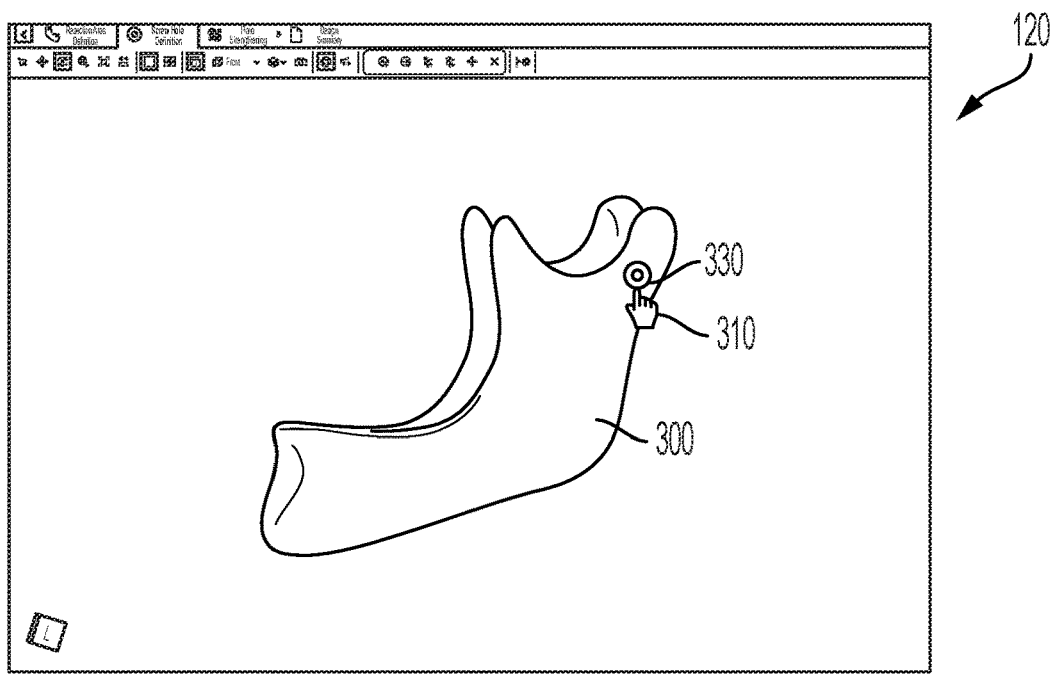
FIGS. 4A-4F are schematic diagrams illustrating an exemplary operation of designing a surgeon specific plate having a plurality of apertures for receiving a bone fastener.
Figure 4B:
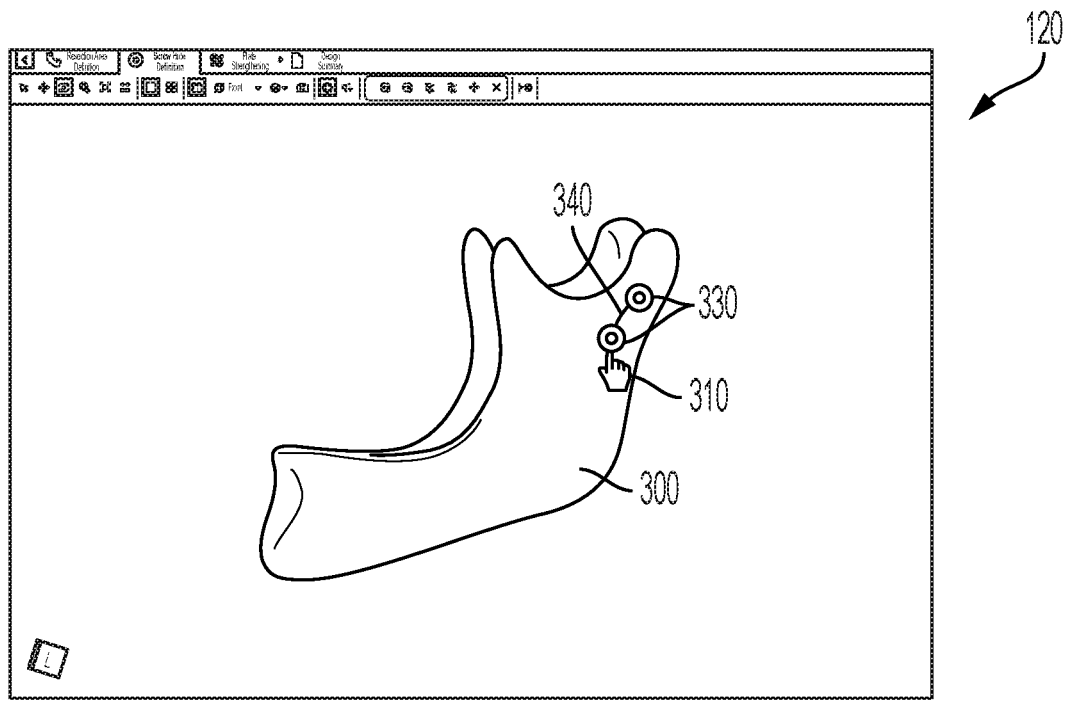
Figure 4C:
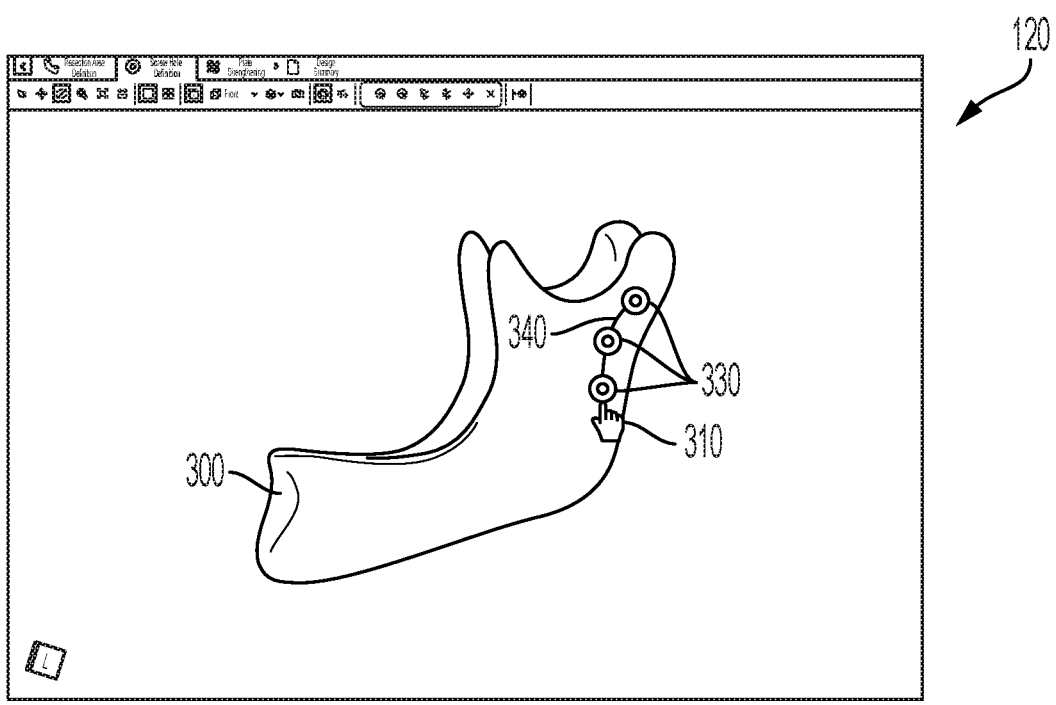
Figure 4D:
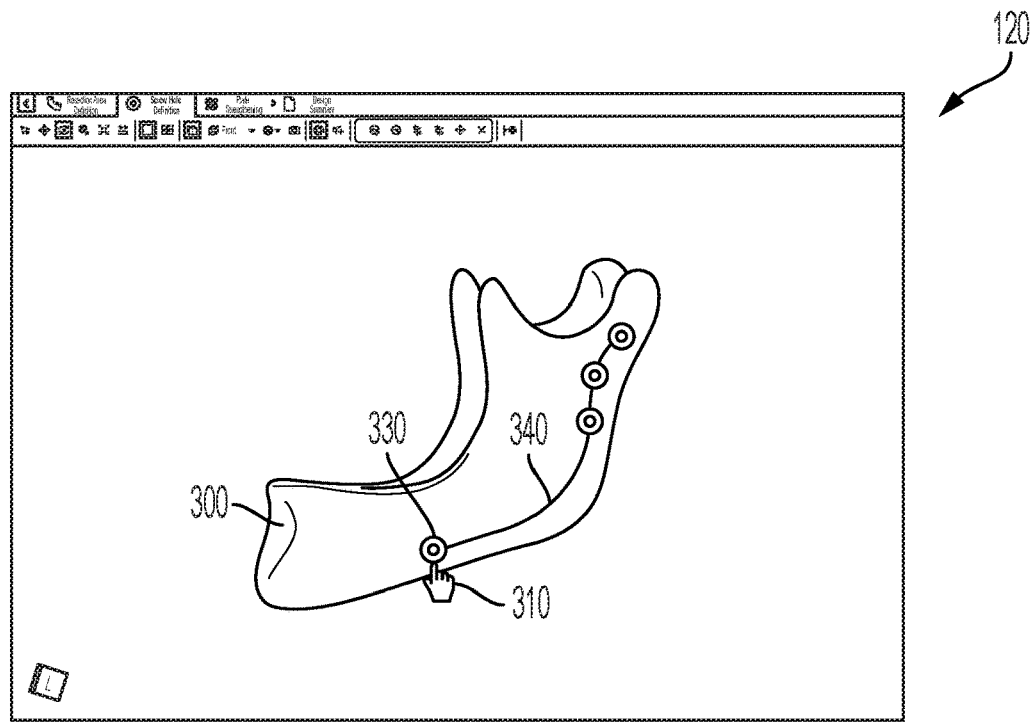
Figure 4E:
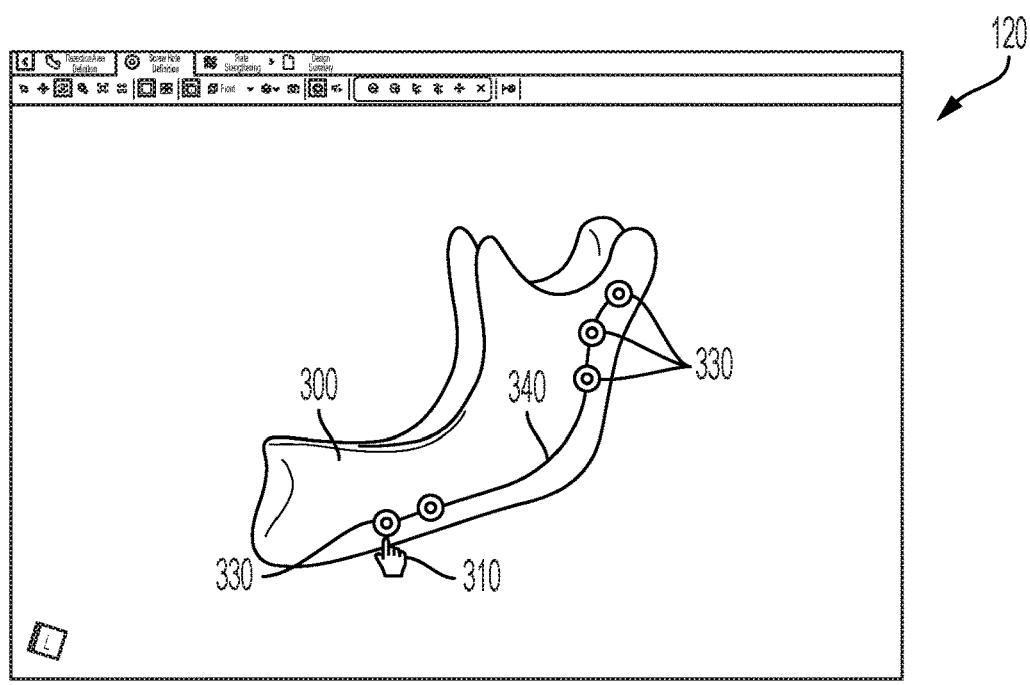
Figure 4F:
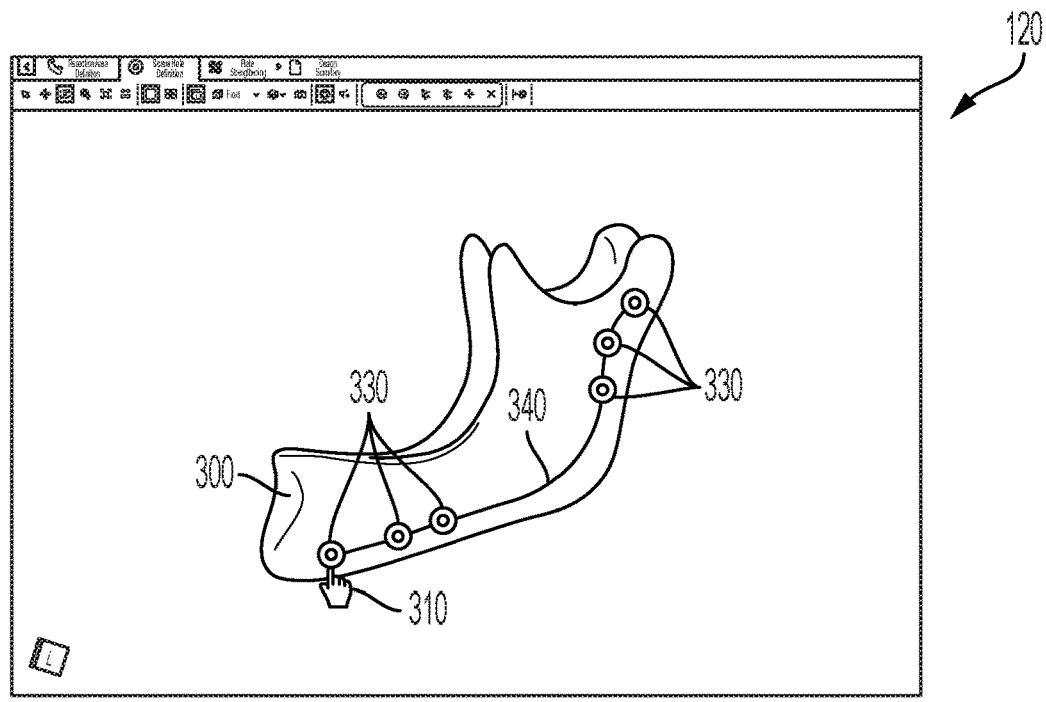

As is known in the art, mandibular reconstruction plates comprise a plurality of apertures or fixation openings. Bone fixation members (such as bone screws or bone pegs) are inserted into the fixation openings for securing the plate to bone. The plate design functionality is configured to allow a user to position a plurality of fixation openings relative to the virtual model 300 of the displayed mandible bone (FIG. 3). With reference to FIG. 4A, the user moves pointer 310 to a desired (virtual) position of a fixation opening, relative to virtual model 300 in a first step. Once the desired position has been reached, a key or button of the input device 150 is pressed. Pressing of the key or button with the pointer 310 being positioned at the desired position of the fixation opening is an input operation. Specifically, upon pressing the key or button a user interaction signal is generated.

Responsive to the user interaction signal the current position of pointer 310 relative to virtual bone model 300 is determined. Based on the position of pointer 310 relative to virtual bone model 300, a point in the coordinate system of the bone model is determined. The determined point is representative of the center of fixation opening 320 and is confirmed on the display device 120 by superimposing a (virtual) model of a plate ring 330 on the virtual bone model 300 at the selected position. The center of plate ring 330 indicates the selected position. The corresponding plate design data resulting from that definition may be stored in the local storage 116 in the form of coordinates (e.g., in the coordinate system of the virtual bone model 300).

As illustrated in FIGS. 4A-4F, the input operation described above with reference to FIG. 4A may be repeated multiple times to define multiple points relative to virtual bone model 300. Again, the position of each point defines the center of a fixation opening 320 and is visualized by an associated plate ring 330 on display device 120.

With reference to FIGS. 4B-4F, a curve 340 in the form of a spline is visualized as soon as two points (i.e., the positions of two fixation openings 320) have been defined relative to bone model 300. The curve 340 is newly calculated and extended as additional fixation openings 320 are defined. The curve 340 (and its underlying point sequence) describes the general extension of the bone plate design and may be stored in the form of plate design data (e.g., as coordinates) in the local storage.

The plate design functionality may be configured to permit a manipulation of the one or more of the fixation openings 320. The fixation openings 320 may be manipulated under control of the input device 150 via the pointer 310. The manipulation may comprise a deletion, insertion or shifting of fixation openings 320 (and the underlying points comprised by the plate design data). The plate design data may be adapted in accordance with the manipulation. As an example, if one of the visualized fixation openings 320 is removed, the corresponding point in the plate design data is removed as well. In one optional implementation, the extension of the curve 340 may also be manipulated using pointer 310.

Figure 5:
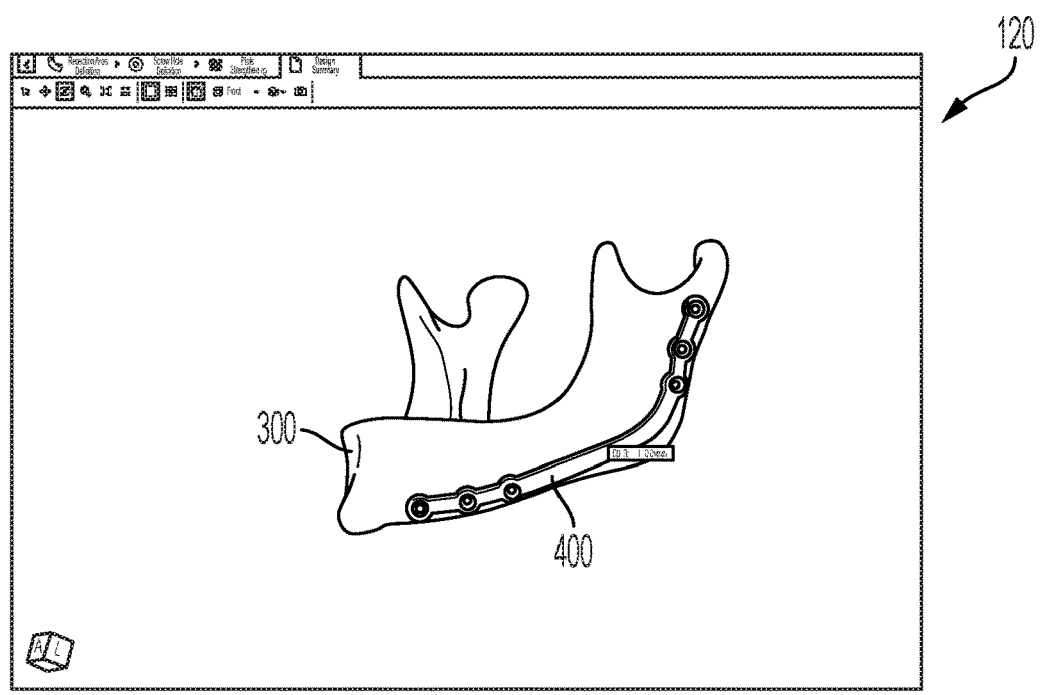
FIG. 5 is a schematic diagram illustrating a designed model of a plate overlaid on the virtual mean model of the mandible bone.

A section of curve 340 between two adjacent fixation openings 320 is representative of a plate segment interconnecting the two associated plate rings 330. By manipulating the position of one of the plate rings 330, the interconnecting segment starting or ending at the corresponding fixation opening 320 (and thus the associated plate segment) is manipulated as well. The interconnecting segment may have a width less than a width of the plate across the fixation openings 320 or greater than the width of the plate across the fixation openings. Each interconnecting segment part of the plate may have the same width as one another, may have the same width as one or more other segment, or each may have a different width from one another. FIG. 5 shows a plate 400 with five interconnecting segments each with approximately the same width as one another.

Once the locations of all fixation openings 320 have been defined (and, if necessary manipulated), a (virtual) model of the plate 400 is visualized. The virtual model of plate 400 is superimposed on the virtual model 300 of the mandible as illustrated in FIG. 5. The virtual model of plate 400 is generated from a combination of generic plate parameters and the plate design data. The generic plate parameters describe generic properties of the plate, such as the diameter of the fixation opening 320, the width and the thickness of the plate ring 330 surrounding the fixation opening 320, and the width and the thickness of a plate segments interconnecting two adjacent fixation openings.

In an optional step, the plate design functionality permits a manipulation of these generic plate parameters. For example, the width of an individual plate segment may be increased or decreased (e.g., step-wise) via the pointer 310 under control of the input device 150. In this manner, the plate can be strengthened in dedicated areas as desired.

Once the input of the plate design data via the plate design functionality is finished, a data set is generated by the processor 114 that defines the plate design. The processor 114 then generates the data set from the plate design data input by the user and the shape data determined from the contours of the mean model. The resulting data set that geometrically defines the dimensions of the plate design can be stored in a dedicated data base or a data file. The data set may also be sent as a data signal via the computer network 160. This process is then repeated until the plate design data has been created for each of the plurality of the virtual models, for example, the small virtual model corresponding to the mean model of the small mandible, the medium virtual mean model corresponding to the mean model of the medium mandible and the large virtual mean model corresponding to the mean model of the large mandible. It will be appreciated that the each of the designs may be different from one another as a surgeon may have slightly different techniques and approaches for reconstructing a relatively small mandible than the surgeon would have for reconstructing a relatively large mandible, and therefore, may desire to place the fixation openings in different locations based upon these different approaches.

Each of the resulting data sets may then be transmitted to the manufacturing device 140 so that an actual plate can be manufactured. The plate may be manufactured from metal (such as titanium). A metallic material is particularly suited for reconstruction plates that typically experience high loads. Other plate embodiments, for example for covering cranial openings, may be manufactured from one or more polymers (such as PMMA and PEEK).

Figure 6A:
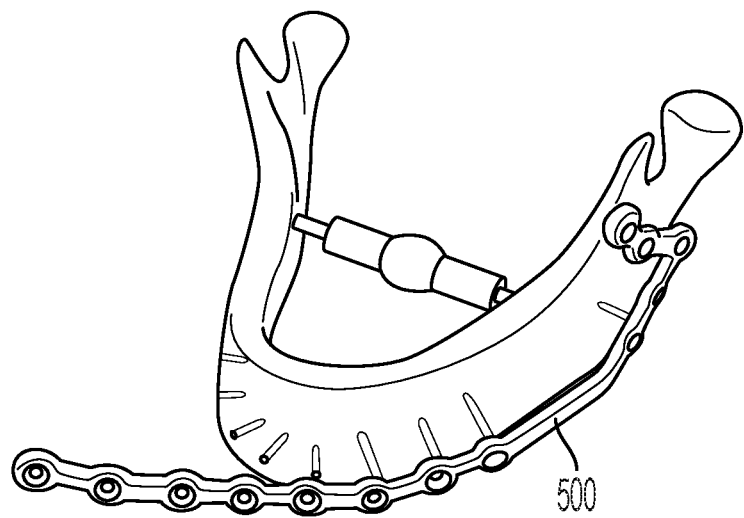
FIGS. 6A and 6B are perspective views showing the manufactured surgeon specific plates being bent around a physical model.
Figure 6B:
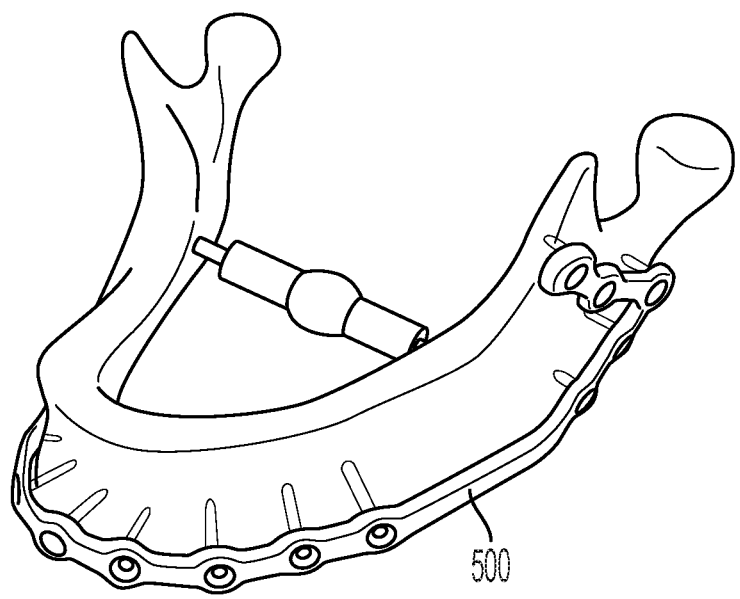

In one embodiment, each of the plates is machined as a planar plate. After plates 500 have been machined, the small plate is bent around a physical model of the small mean model mandible, the medium plate is bent around a physical model of the medium mean model mandible and the large plate is bent around a physical model of the large mean model mandible in order to pre-shape or contour each of the plates as shown in FIG. 6A (illustrating an anatomically pre-shaped plate including an incomplete bend in which a bending stop is chosen at a predetermined point that is preferably adjacent the chin) and in FIG. 6B (illustrating an anatomically pre-shaped plate that is bent completely around the physical model). In another embodiment, manufacturing device 140 may mold each of the plates 500 to the contour of the mean model such that the bending step is not required. Another manufacturing process that may be used to create a plate that does not have to be pre-contoured as much as a flat plate is three-dimensional milling. After each of the surgeon-specific plates 500 have been contoured, the plates may be shipped to the hospital.

Figure 7:
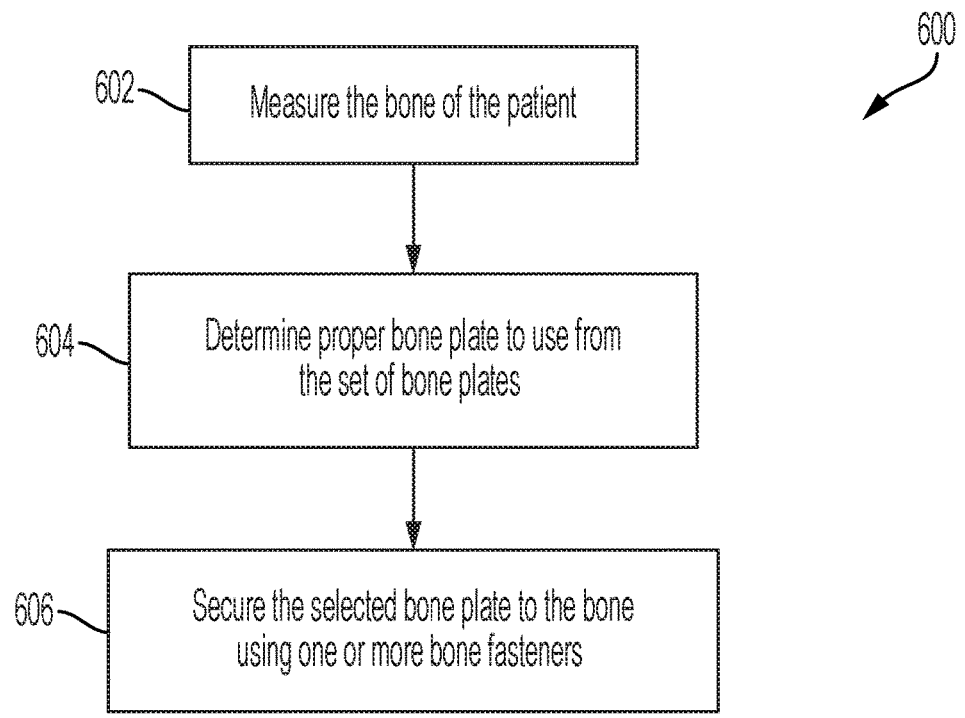
FIG. 7 is a flow diagram illustrating a method of repairing a fractured bone using the surgeon specific plates.
Figure 8:
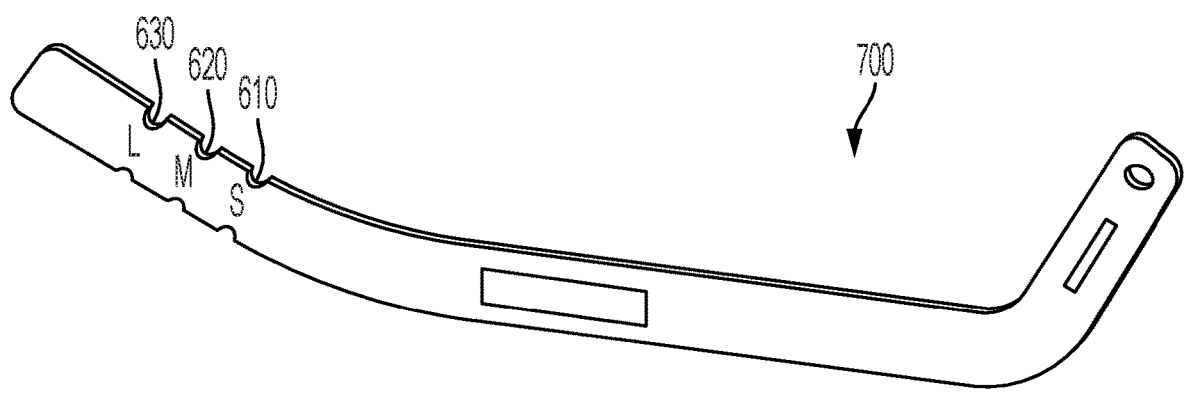
FIG. 8 is a front elevation view of a sizer adapted to determine the size of a mandible of a particular patient.

Reconstruction of a mandible of a patient 600 will now be described with reference to FIG. 7. Prior to reconstruction surgery, the surgeon-specific small plate, the surgeon-specific medium plate and the surgeon-specific large plate will be placed in the operating room for the surgeon. The surgeon may then expose the mandible of the patient and use a sizer 700 to determine the size of the mandible of the patient 602. Sizer 600, as shown in FIG. 8, may be a flexible tape-like device that is generally L-shaped to conform to the mandible of the patient. Sizer 700 includes a plurality of markings 710, 720, 730. In this exemplary embodiment, marking 710 denotes that the small plate should be used because the mandible of the patient is within the smallest class of the population, while marking 720 denotes that the medium plate should be used because the mandible of the patient is within the middle class of the population and marking 730 denotes that the large plate should be used because the mandible of the patient is within the largest class of the population. After the proper plate has been determined 604, the surgeon may fixate the selected plate to the patient as he or she normally would using one or more bone fasteners 606. The surgeon-specific design of the plate allows the surgeon to fasten the plate to the mandible in accordance with the surgeon's individualized techniques and approaches while the anatomically pre-shaped plate generally conforms to the mandible of the patient and minimizes the required intraoperative manipulation necessary to properly fit and secure the plate to the mandible of the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of designing a set of contoured implants for fixation to a bone of a patient, comprising:
   obtaining a set of virtual bone models of the bone;
   selecting a plurality of points on an outer surface of each virtual bone model in the set of virtual bone models;
   manufacturing a set of implants, each implant corresponding to a respective virtual bone model and having fixation holes corresponding to the selected plurality of points on the outer surface of the respective virtual bone model;
   contouring each implant in the set of implants; and
   selecting a contoured implant from the set of implants for fixation to the bone of the patient, wherein the selected contoured implant corresponds to a size of the bone of the patient.

2. The method of claim 1, wherein each virtual model in the set of virtual models is an anatomical mean model.

3. The method of claim 1, further comprising:
   determining the size of the bone of the patient using a sizer to select the contoured implant from the set of implants.

4. The method of claim 1, wherein each virtual bone model in the set of virtual bone models vary in size.

5. The method of claim 1, further comprising:
   creating a virtual implant model for each virtual bone model in the set of virtual bone models based upon the selected plurality of points.

6. The method of claim 5, wherein each manufactured implant in the set of implants corresponds to a respective virtual implant model.

7. The method of claim 1, further comprising:
   manufacturing a set of physical bone models, each physical bone model corresponding to a respective virtual bone model in the set of virtual bone models.

8. The method of claim 7, wherein each implant in the set of implants is contoured to a respective physical bone model from the set of physical bone models.

9. The method of claim 8, wherein contouring each implant in the set of implants includes bending each implant around the respective physical bone model.

10. The method of claim 1, wherein the obtained set of virtual bone models includes at least a small, medium and large virtual bone models.

11. A method of designing a set of contoured implants for fixation to a bone of a patient, comprising:
    obtaining at least three different sized virtual bone models of the bone;
    selecting a plurality of points on an outer surface of each virtual bone model;
    manufacturing implants, each implant corresponding to a respective virtual bone model and having fixation holes corresponding to the selected plurality of points on the outer surface of the respective virtual bone model;
    contouring each of the manufactured implants; and
    selecting a contoured implant for fixation to the bone of the patient, wherein the selected contoured implant corresponds to a size of the bone of the patient.

12. The method of claim 11, wherein each virtual bone model is an anatomical mean model.

13. The method of claim 11, further comprising:
   determining the size of the bone of the patient using a sizer to select the contoured implant.

14. The method of claim 11, wherein the bone of the patient is a mandible.

15. The method of claim 11, further comprising:
   creating a virtual implant model for each virtual bone model based upon the selected plurality of points.

16. The method of claim 15, wherein each manufactured implant corresponds to a respective virtual implant model.

17. The method of claim 11, further comprising:
   manufacturing a set of physical bone models each corresponding to a respective virtual bone model.

18. The method of claim 17, wherein each implant is contoured to a respective physical bone model.

19. The method of claim 18, wherein contouring each implant includes bending each implant around the respective physical bone model.

20. The method of claim 11, wherein the at least three differently sized virtual bone models include at least small, medium and large virtual bone model sizes.

* * * * *